United States Patent
Shelton, IV (10) Patent No.: US 7,246,734 B2
(45) Date of Patent: Jul. 24, 2007

(54) ROTARY HYDRAULIC PUMP ACTUATED MULTI-STROKE SURGICAL INSTRUMENT

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 37 days.

(21) Appl. No.: 11/294,584

(22) Filed: Dec. 5, 2005

(65) Prior Publication Data

US 2007/0125826 A1   Jun. 7, 2007

(51) Int. Cl.
*A61B 17/068* (2006.01)
(52) U.S. Cl. .................. 227/175.1; 227/19; 606/219
(58) Field of Classification Search ............. 227/19, 227/175.1, 176.1, 179.1, 156; 606/219, 142, 606/167
See application file for complete search history.

(56) References Cited

U.S. PATENT DOCUMENTS

| | | | | |
|---|---|---|---|---|
| 4,175,314 A * | 11/1979 | Spehrley, Jr. .............. 29/432.1 |
| 4,472,117 A * | 9/1984 | Wenstrup .................. 417/477.2 |
| 5,411,508 A * | 5/1995 | Bessler et al. ............. 606/153 |
| 5,465,895 A | 11/1995 | Knodel et al. |
| 5,609,285 A * | 3/1997 | Grant et al. ............. 227/179.1 |
| 5,658,300 A * | 8/1997 | Bito et al. .................. 606/143 |
| 5,782,397 A * | 7/1998 | Koukline .................. 227/176.1 |
| 6,126,651 A * | 10/2000 | Mayer ............................ 606/1 |
| 6,264,086 B1 * | 7/2001 | McGuckin, Jr. ......... 227/180.1 |
| 6,506,196 B1 * | 1/2003 | Laufer ........................ 606/142 |
| 6,508,809 B1 * | 1/2003 | Bacher .......................... 606/1 |
| 6,588,626 B2 | 7/2003 | Sauer et al. |
| 6,755,338 B2 | 6/2004 | Hahnen et al. |
| 6,830,174 B2 | 12/2004 | Hillstead et al. |
| 6,905,057 B2 | 6/2005 | Swayze et al. |
| 6,964,363 B2 * | 11/2005 | Wales et al. ............. 227/175.1 |
| 6,988,649 B2 * | 1/2006 | Shelton et al. ........... 227/175.2 |
| 2004/0243176 A1 | 12/2004 | Hahnen et al. |

\* cited by examiner

*Primary Examiner*—Scott A. Smith (57) ABSTRACT

A surgical instrument (e.g., endocutter, grasper, cutter, staplers, clip applier, access device, drug/gene therapy delivery device, and energy device using ultrasound, RF, laser, etc.) may benefit from having a plurality of hydraulically actuated subsystems (e.g., severing, stapling, articulation, locking/unlocking, lockout enabling/disabling, grasping, etc.) supplied with hydraulic power from a trigger actuated rotary pump (e.g., lobe pump, rotary gear pump, internal rotating gear pump, flexible vane rotor pump, rotary vane pump). Thereby, an available amount of mechanical advantage available at a firing trigger may be optimally distributed to various end effector components, perhaps sequenced by an electroactive polymer or piezoelectrically actuated function switch block.

20 Claims, 11 Drawing Sheets

ROTARY HYDRAULIC PUMP ACTUATED MULTI-STROKE SURGICAL INSTRUMENT

FIELD OF THE INVENTION

The present invention relates in general to surgical instruments that have an end effector or surgical implement that is capable of being endoscopically or laparoscopically inserted, perhaps through a cannula of a trocar, and proximally controlled via fluid transfer through an elongate and perhaps articulating shaft.

BACKGROUND OF THE INVENTION

Endoscopic and laparoscopic surgical instruments are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler with a single firing stroke, thereby severing and stapling the tissue. The simultaneous severing and stapling avoids complications that may arise when performing such actions sequentially with different surgical tools that respectively only sever or staple.

Generally, a single closing stroke followed by a single firing stroke is a convenient and efficient way to perform severing and stapling. However, in some instances, it would be desirable for multiple firing strokes to be required. For example, surgeons are able to select from a range of jaw sizes with a corresponding length of staple cartridge for the desired length of cut. Longer staple cartridges require a longer firing stroke. Thus, a hand-squeezed trigger to effect the firing is required to exert a larger force for these longer staple cartridges in order to sever more tissue and drive more staples as compared to a shorter staple cartridge. It would be desirable for the amount of force to be lower and comparable to shorter cartridges so as not to exceed the hand strength of some surgeons. In addition, some surgeons not familiar with the larger staple cartridges may become concerned that binding or other malfunction has occurred when an unexpectedly higher force is required.

In U.S. Pat. No. 6,905,057, a multiple firing stroke handle for an endoscopic surgical stapling and severing instrument succeeds in reducing these firing forces by advancing a firing mechanism during each squeeze of the firing trigger, mechanically coupling this firing motion through a pawl into a linked rank. In addition to reducing the force required to squeeze the firing trigger, the linked rack stows into a pistol grip of the handle to advantageously reduce the length of the handle as compared to a rigid rack.

In U.S. Pat. Nos. 6,755,338 and 6,830,174, an alternative approach has been proposed with a trigger driven master hydraulic piston and cylinder arrangement in an instrument handle that transmits fluid pressure through a shaft to a slave cylinder to hydraulically actuate an end effector. Incorporating several small and flexible hydraulic lines into such an instrument benefits from the internal pressures being balanced and not requiring a complex support structure and sheathing as perhaps a mechanical beam would, especially through an articulating shaft.

While such hydraulically actuated surgical instruments may support multiple axis articulation, simplified fabrication, and reduced size, design limitations persist. In particular, the fluid transferred from a hydraulic master cylinder in the handle is received in a corresponding slave cylinder in the end effector. Thus, the tuned volume of fluid transferred and the internal pressure imparted to this fluid are constrained by the available volume in the end effector. In addition, with increased internal pressures to obtain effective actuation with a reduced fluid volume, dynamic seals between the hydraulic piston and cylinder are challenged. Avoiding leaks with tighter seals, however, increases the internal frictional resistance that the surgeon must overcome in actuating the instrument.

Consequently, a significant need exists for an improved surgical stapling instrument that uses multiple firing strokes to hydraulically actuate an end effector.

BRIEF SUMMARY OF THE INVENTION

The invention overcomes the above-noted and other deficiencies of the prior art by providing a trigger actuated rotary pump in a handle of a surgical instrument that provides the motive power to a fluid control system that actuates an end effector via fluid conduits contained in an elongate shaft. Thereby, a desirable degree of mechanical advantage may be incorporated into the relationship between a user actuated trigger and the power output of the rotary pump.

In one aspect of the present invention, a surgical instrument has a hydraulic actuator positioned in an elongate implement portion that is attached to a handle. A hand actuator is attached to the handle for movement to operate a rotary pump contained in the handle to transfer fluid between a reservoir and the hydraulic actuator to remotely actuate the implement portion.

In another aspect of the present invention, a surgical instrument has a plurality of hydraulic actuators positioned in an elongate implement portion. A fluid control system with a hydraulic switching apparatus selectively couples hydraulic pressure from a rotary pump in a handle through selected hydraulic conduits to each of the plurality hydraulic actuator for sequenced operation of the implement portion.

In yet another aspect of the present invention, a surgical instrument with a plurality of hydraulic actuators positioned in an elongate implement portion are powered by a rotary pump that is selectively coupled by a hydraulic switching apparatus in accordance to circuitry.

These and other objects and advantages of the present invention shall be made apparent from the accompanying drawings and the description thereof.

DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
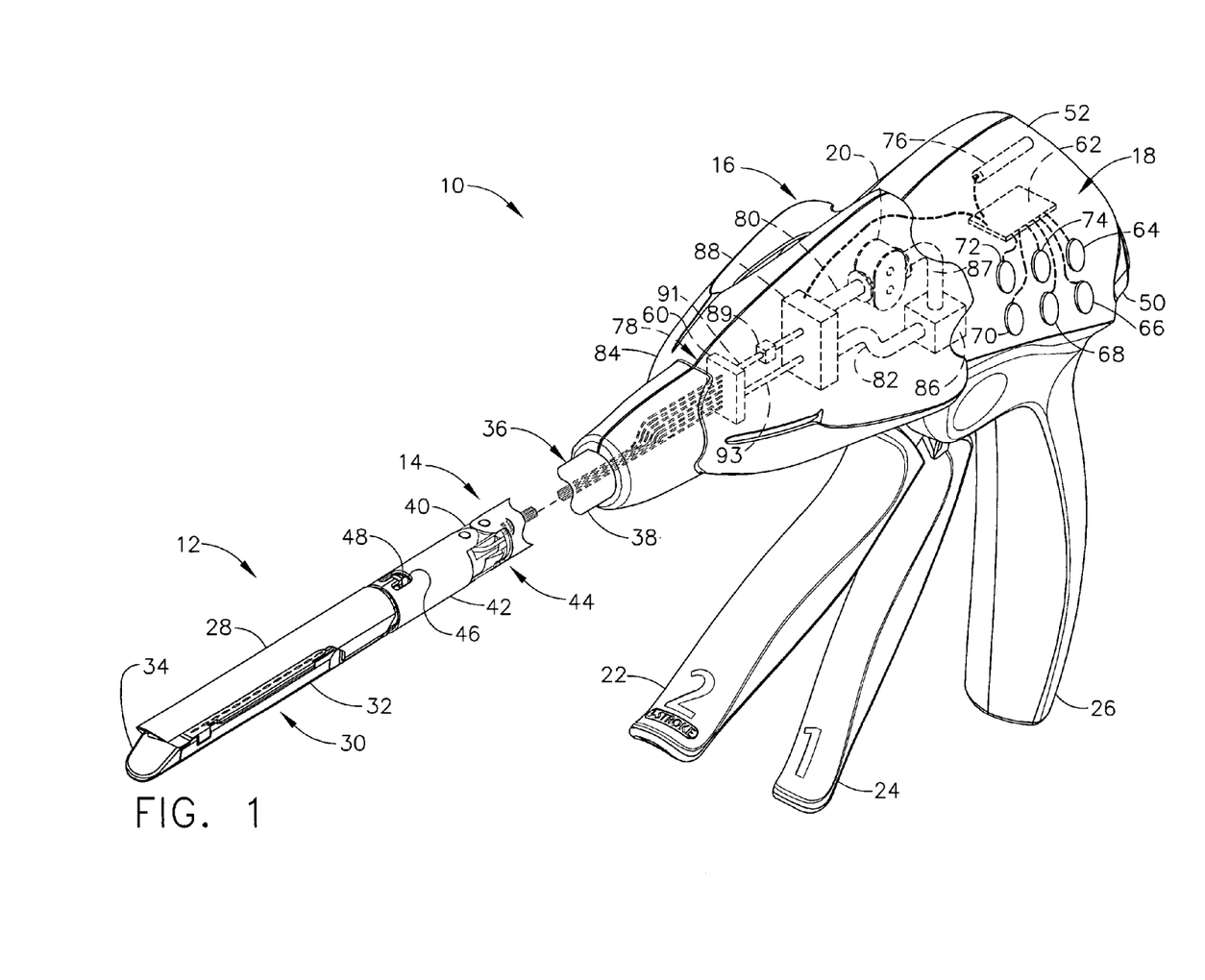
FIG. 1 is a front left isometric view of a surgical stapling and severing instrument with a rotary pump driven fluid control system depicted in phantom.

Turning to the Figures, wherein like numerals denote like components throughout the several views, in FIG. 1, a surgical instrument is depicted as a surgical stapling and severing instrument 10 that has a surgical implement (end effector), depicted as a staple applying assembly 12, that may be endoscopically or laparoscopically inserted, perhaps through a cannula of a trocar (not shown), and proximally controlled via fluid transfer through an elongate, and perhaps articulating, shaft 14 by a fluid control system 16 contained in a handle 18. Advantageously, a rotary pump 20 consistent with aspects of the invention is driven by multiple strokes of a firing trigger 22 optimized for a desired mechanical advantage to maximize the amount of energy the user may impart per stroke to perform one or more actuation motions at the staple applying assembly 12.

It will be appreciated that the terms "proximal" and "distal" are used herein with reference to a clinician gripping a handle of an instrument. Thus, the staple applying assembly 12 is distal with respect to the more proximal handle 18. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The handle 18 has a closure trigger 24 proximal to the firing trigger 22 that is first drawn toward a pistol grip 26 to grasp tissue, pivoting an upper jaw (anvil) 28 toward a lower jaw 30 of the staple applying assembly 12 into a closed position. The lower jaw 30 includes an elongate staple channel 32 that holds a replaceable staple cartridge 34. This closure is effected by converting the pivoting movement of the closure trigger 24 to a distal translation of an outer closure sleeve 36 of the elongate, articulating shaft 14 to pivot shut the anvil 28. In particular, a proximal closure sleeve tube 38 is attached via top and bottom double pivoting links 40 to a distal closure tube 42 for articulating movement across an articulation joint 44. A horseshoe shaped recess 46 on the distal closure tube 42 engages an anvil feature 48 of the anvil 28 that extends proximally to the lateral pivoting engagement between the anvil 28 and the elongate staple channel 32.

Upon further depression of the closure trigger 24, a closure release button 50 extends outwardly from an aft surface of a handle housing 52 of the handle 18 as an internal locking mechanism (not shown) locks the closure trigger 24 in the clamped position. Depression of the closure release button 50 unlocks the closure trigger 24 unless precluded by certain locks related to incomplete firing.

The fluid control system 16 may selectively control a plurality of hydraulic subsystems (e.g., staple drivers, cutting knife, lockout device, etc.) with a valve unit, depicted as a function switch block 60, which may include any kind of valve or valves suitable for controlling and directing the flow of hydraulic fluid. For instance, the function switch block 60 may include electrically actuated valves, such as, for example, piezoelectric valves or Electro Active Polymer (EAP) valves which may be configured in response to an electrical signal from control circuitry 62 in response in turn to an input received from input buttons, such as buttons 64, 66, 68, 70, 72, and/or 74. An electrical power source (e.g., lithium hydride chemical battery, charged ultra-capacitor) 76 may provide electrical power to the control circuitry 62 and buttons 64, 68, 70, 72, 74. The control circuitry 62 may be any kind of circuit capable of generating signals for configuring function switch block 60 in response to input from buttons 64, 68, 70, 72, 74, for instance a microprocessor and other related components including Random Access Memory (RAM), Read Only Memory (ROM), etc. Alternatively, the control circuitry 62 may include various logical circuit elements such as a programmable logic array.

As an alternative to buttons, sensors may detect an operating parameter (e.g., closure status of jaws, presence and type of staple cartridge 34, position of a tissue severing device, and/or status of staples (i.e., in staple cartridge and unformed or dispensed and formed). The control circuitry 62 may then respond automatically to select, perhaps sequentially, various ones of a plurality of hydraulic conduits (e.g., passages, flexible lines) 78 to receive hydraulic pressure from a discharge line 80 from the rotary pump 20. Each hydraulic subsystem may have dedicated return lines of the plurality of hydraulic conduits 78 or check valves for isolation from other hydraulic subsystems before being ported to a return line 82. The hydraulic conduits 78 may allow for a rotation knob 84 to rotate the elongate, articulated shaft 14. The return line 82 ports fluid into a reservoir 86 that in turn directs fluid through an intake line 87 to the rotary pump 20.

Each input button 64, 66, 68, 70, 72, 74 may correspond to a particular surgical implement, or portion of a surgical implement 12, included in the staple applying assembly 34. For example, button 64 may correspond to a cutter while buttons 68, 70, 72, 74 may each correspond to a zone of staples (not shown). Selecting the button 68, 70, 72, 74 corresponding to a hydraulic subsystem may cause the control circuitry 62 to configure the function switch block 60 such that a hydraulic device corresponding to the function is fired when firing trigger 22 is depressed, driving the corresponding hydraulic subsystem. Multiple buttons 68, 70, 72, 74 may be selected to create firing patterns including more than one hydraulic subsystem. Alternatively, each input button 64, 66, 68, 70, 72, 74 may represent a pre-determined firing order and/or pattern. For example, selecting a button 64, 68, 70, 72, 74 may cause the control circuitry 62 to configure the function switch block 60 such that hydraulic subsystems are fired when the firing trigger 22 is depressed.

One of the buttons 64, 66, 68, 70, 70, 72, 74 may disable the fluid control system 16 by directing the fluid from the discharge line 80 to be routed directly back from the function switch block 60 to the return line 82 to the reservoir 86. Alternatively or in addition, a default unpowered state may result in this operation. To that end, a return valve body 88 is interposed between the discharge and return lines 80, 82 as well as a check valve 89 inserted into a feed line 91 between the return valve body 88 and the function switch block 60. A return line 93 also communicates from the function switch block 60 and the return valve body 88. The check valve 89 may be selectively opened by an electroactive polymer actuator or a piezoelectric actuator responsive to the control circuitry 62.

As a further alternative, the control circuitry 62 may configure the function switch block 60 to introduce a delay to the driving of one or more hydraulic subsystems included in the staple applying assembly 34. For example, it may be desirable to drive a cutting implement and then delay for a predetermined time before driving one or more zones of a stapling implement 12. The delay may be accomplished according to any suitable method. For instance, the control circuitry 62 may configure the function switch block 60 to open a path for hydraulic fluid between the rotary pump 20 and a first hydraulic subsystem (not shown) included in the surgical implement 12. When the firing trigger 22 is actuated, the rotary pump 20 may generate pressurized hydraulic fluid, which drives the first hydraulic subsystem. The control circuitry 62 may sense when the first hydraulic subsystem is driven (e.g., by sensing the position of the firing trigger 22). When the first hydraulic subsystem is driven, the control circuitry 62 may begin a timer that counts off a predetermined delay time. At the expiration of the predetermined delay time, the control circuitry 62 may configure the function switch block 60 to provide the pressurized hydraulic fluid to a second hydraulic subsystem (not shown).

It should be appreciated that hydraulic subsystems thus controlled may include a cutting edge that is transversely (vertically) driven up from the elongate staple channel 32 of the lower jaw 30 by a hydraulic cutting bladder or cylinder (s). Alternatively or in addition, one or more hydraulic staple bladders or cylinders positioned between the elongate staple channel 32 and the replaceable staple cartridge 34 may transversely vertically) drive staple drivers that in turn dispense and form staples against an inner surface of the anvil 28.

Figure 2:
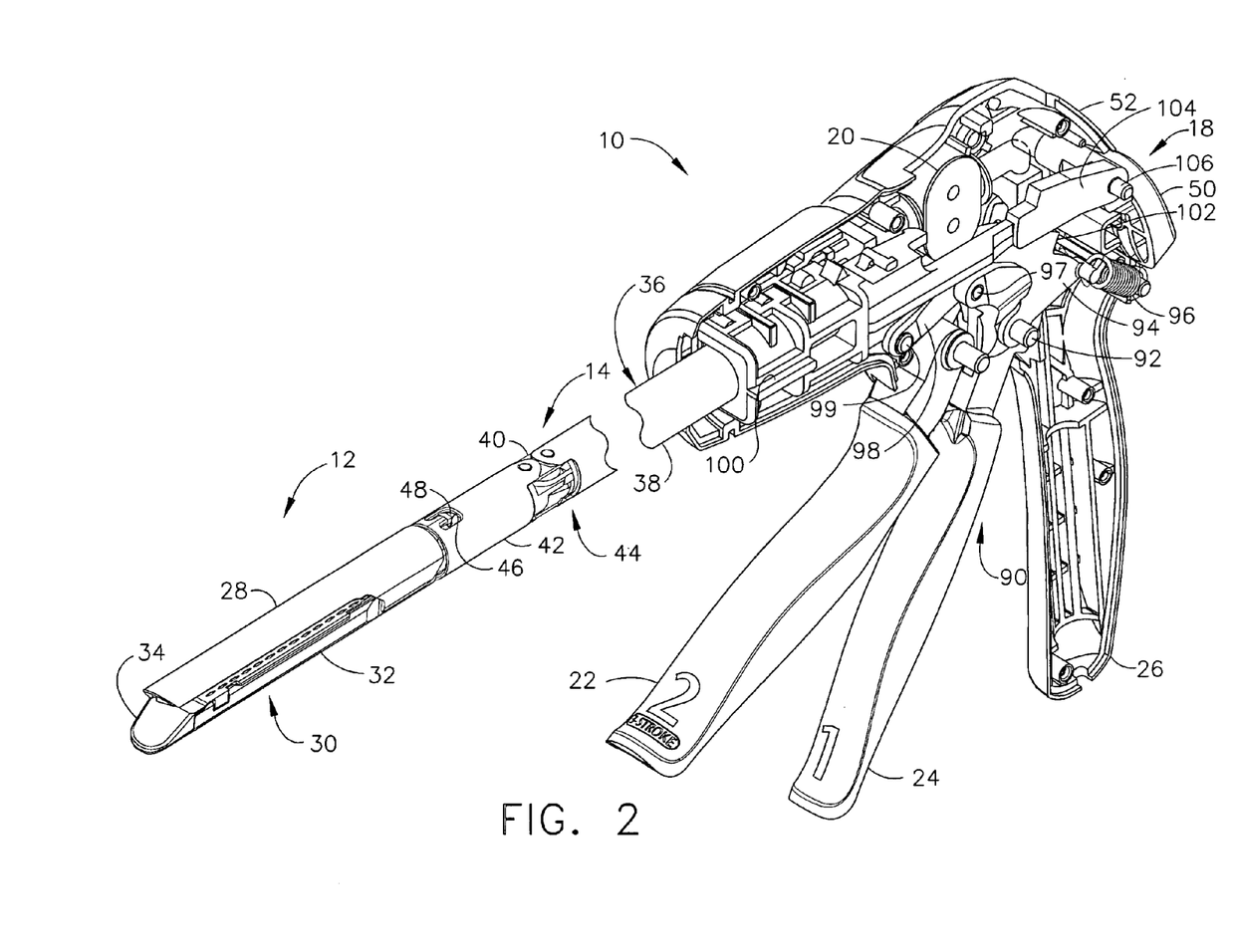
FIG. 2 is a front left isometric view of the surgical stapling and severing instrument of FIG. 1 with omission of a left half of a handle housing, a rotation knob, and portions of the fluid control system other than the rotary pump to expose a mechanical closure mechanism.

In FIG. 2, a left half of the handle housing 52, the rotation knob 84, and the fluid control system 16 are omitted, except for the rotary pump 20, to expose a mechanically operated closure system 90. The closure trigger 24 pivots about a lateral closure pivot pin 92 engaged to the handle housing 52. An upper portion 94 of the closure trigger 24 above the lateral closure pivot pin 92 is proximally biased by a closure trigger return spring 96. As the upper portion 94 distally advances with the depression of the closure trigger 24, a proximal link pin 97 moves a closure link 98 that distally translates a distal link pin 99 that in turn moves a closure yoke 100 that is engaged to the outer closure sleeve 36. As the closure trigger 24 approaches full depression, an aft notched surface 102 on the upper portion 94 receives a downwardly rotating arm 104 that is attached at a release button lateral pivot 106, which engages the handle housing 52 for rotation. The closure release button 50 is also attached to the release button lateral pivot 106 and rotates outwardly.

The mechanically operated closure system 90 is described in greater detail in a co-pending and commonly owned U.S. patent application Ser. No. 10/955,042, "Articulating Surgical Stapling Instrument Incorporating a Two-Piece E-Beam" to Wales et al., filed on 30 Sep. 2004, the disclosure of which is hereby incorporated by reference in its entirety. Alternatively, the rotary pump 20 may provide the closure motive force for a fluid controlled anvil, such as described in co-pending and commonly owned U.S. patent application Ser. No. 11/165,094, "Surgical Instrument Having Fluid Actuated Opposing Jaws" to Wales, filed 23 Jun. 2005, the disclosure of which is hereby incorporated by reference in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Figure 3:
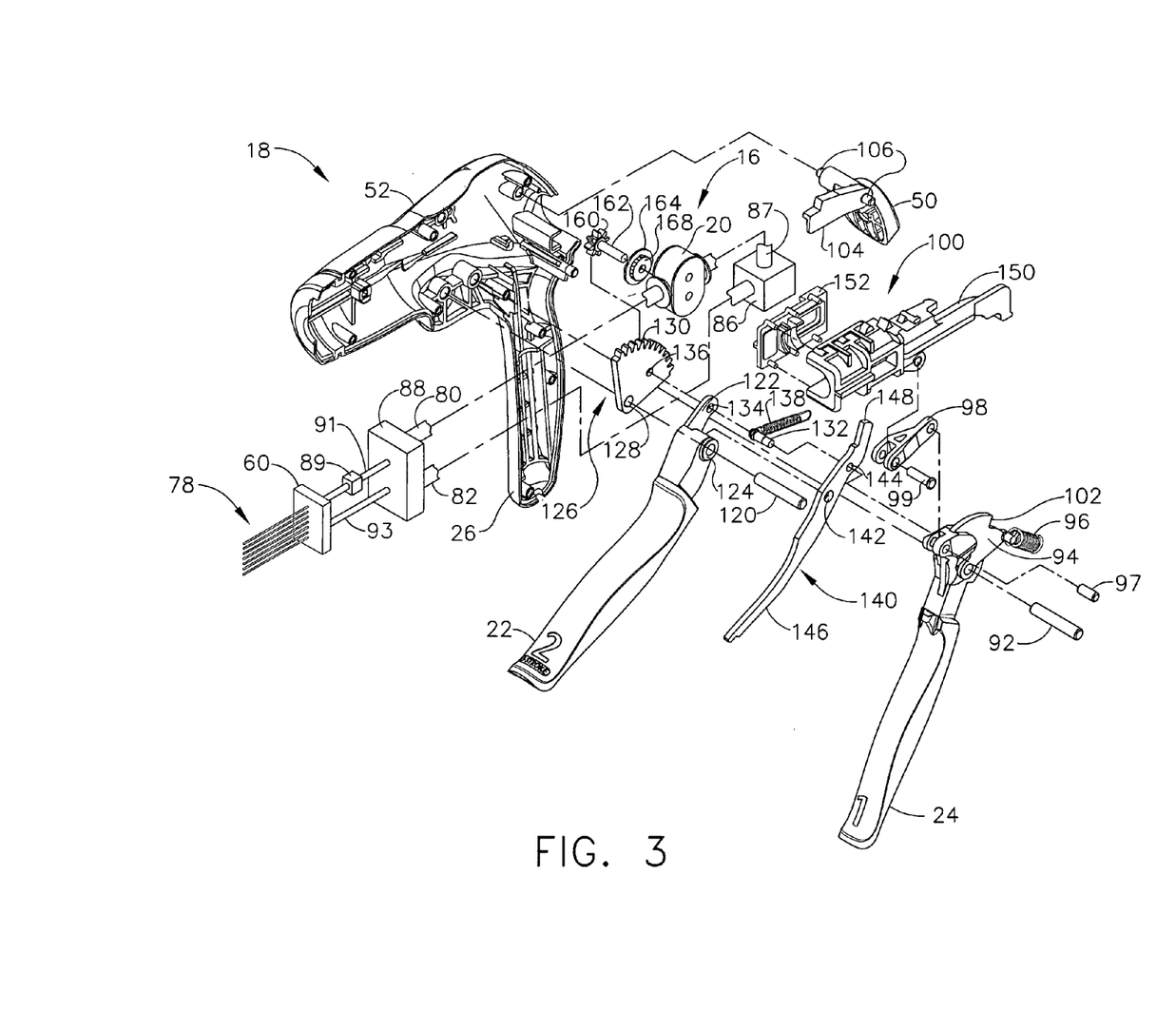
FIG. 3 is a front left isometric exploded view of the handle of the surgical instrument of FIG. 2 with a left half of the handle housing omitted.

In FIG. 3, the firing trigger 22 rotates about a firing trigger lateral pivot pin 120 that is engaged within the handle housing 52. A gear connection arm 122 extends upwardly and proximally from a right side of an axle hub portion 124 of the firing trigger 22 that receives the firing trigger lateral pivot pin 120. A drive gear 126 positioned on a right side of the axle hub portion 124, has an angled corner through hole 128 that receives the firing trigger lateral pin 120. A gear segment 130 is positioned opposite and equidistant to the angled corner through hole 128. A closure trigger linkage pin 132 passes through an upper through hole 134 in the gear connection arm 122 and an upper through hole 136 in the drive gear 126. Between the drive gear 126 and gear connection arm 122, a compression spring 138 has one end received by the closure trigger linkage pin 132 and another end proximally attached to the handle housing 52 to bias the firing trigger 22 distally, resetting the firing trigger 22 between strokes.

A trigger biasing arm 140 has a lower through hole 142 that also receives the firing trigger lateral pivot pin 120 and an upper through hole 144 that receives the closure trigger linkage pin 132. A lower arm portion 146 of the trigger biasing arm 140 is positioned under the firing trigger 22. An upper arm portion 148 of the trigger biasing arm 140 resides under a main body 150 of the closure yoke 100, which is attached to a closure yoke back plate 152 on the right side. It should be appreciated that a distal portion of the closure yoke 100 interferes with the actuation of the firing trigger 22 by blocking the upper arm portion 148 of the trigger biasing arm 140 until the closure yoke 100 is distally advanced and the closure trigger 24 is clamped.

Figure 4:
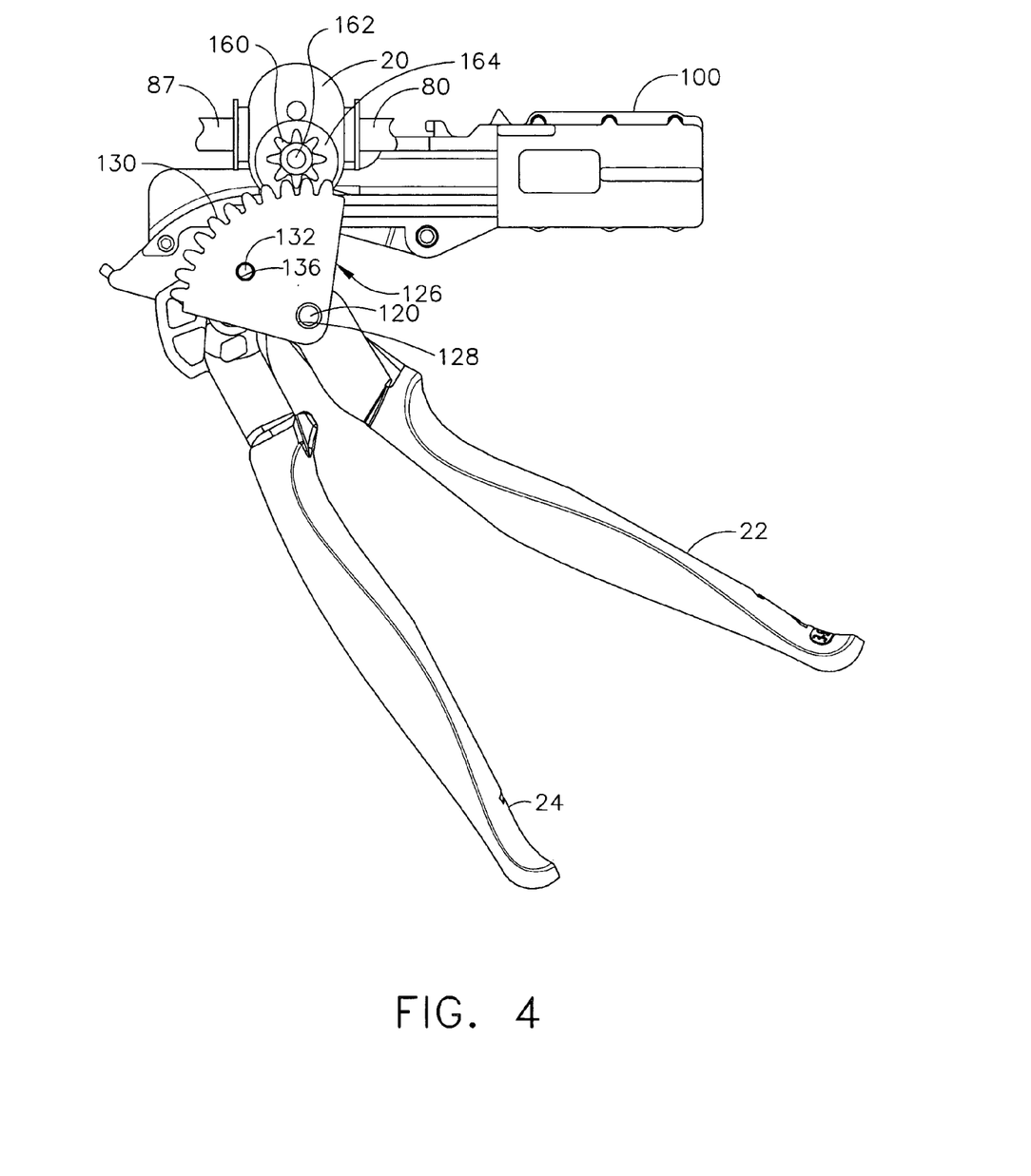
FIG. 4 is a right side view in elevation of a portion of the handle of FIG. 3 including closure and firing triggers, a rotary pump and a closure yoke.
Figure 5:
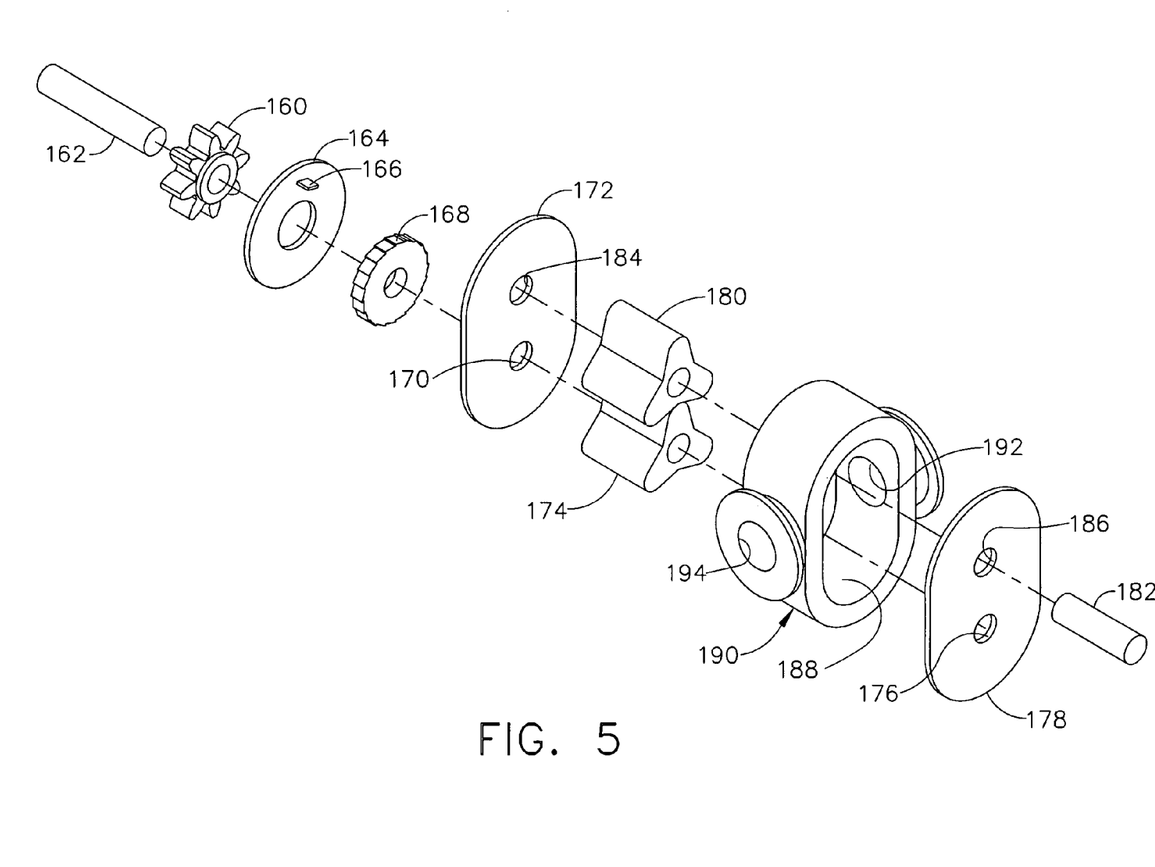
FIG. 5 is an isometric exploded view of the rotary pump of FIG. 1, more particularly a rotary lobe pump.

In FIGS. 3–5, the rotary pump 20 is coupled to the firing trigger 22 during firing strokes by a pump drive gear 160 that engages the gear segment 130 of the drive gear 126. The pump drive gear 160 turns freely about a primary pump shaft 162 that extends to the right through an upper portion of the rotary pump 20. A ratchet cover plate 164 is attached to a left side of the primary drive gear 160 and has an axial opening for receiving the primary pump shaft 162.

With particular reference to FIG. 5, a ratchet pawl 166 extends from a left face of the ratchet cover plate 164, which in the illustrative version is molded from plastic, to selectively engage a ratchet gear 168 that is attached to the primary pump shaft 162 for rotational movement. The primary pump shaft 162 passes through a lower hole 170 in a right-side pump cover plate 172 to pass through and be attached for rotational movement to a primary lobe member 174. A left end of the primary pump shaft 162 is received in a lower hole 176 in a left-side pump cover plate 178. A secondary lobe member 180 rotates on a secondary pump shaft 182 whose right and left ends respectively are received in an upper hole 184 in the right side pump cover plate 172 and an upper hole 186 in the left side pump cover plate 178. Both lobe members 174, 180 reside within an oval pump cavity 188 within a valve body 190 that has an aft port 192 communicating with the intake line 87 and a forward port 194 communicating with the discharge line 80.

Figure 6:
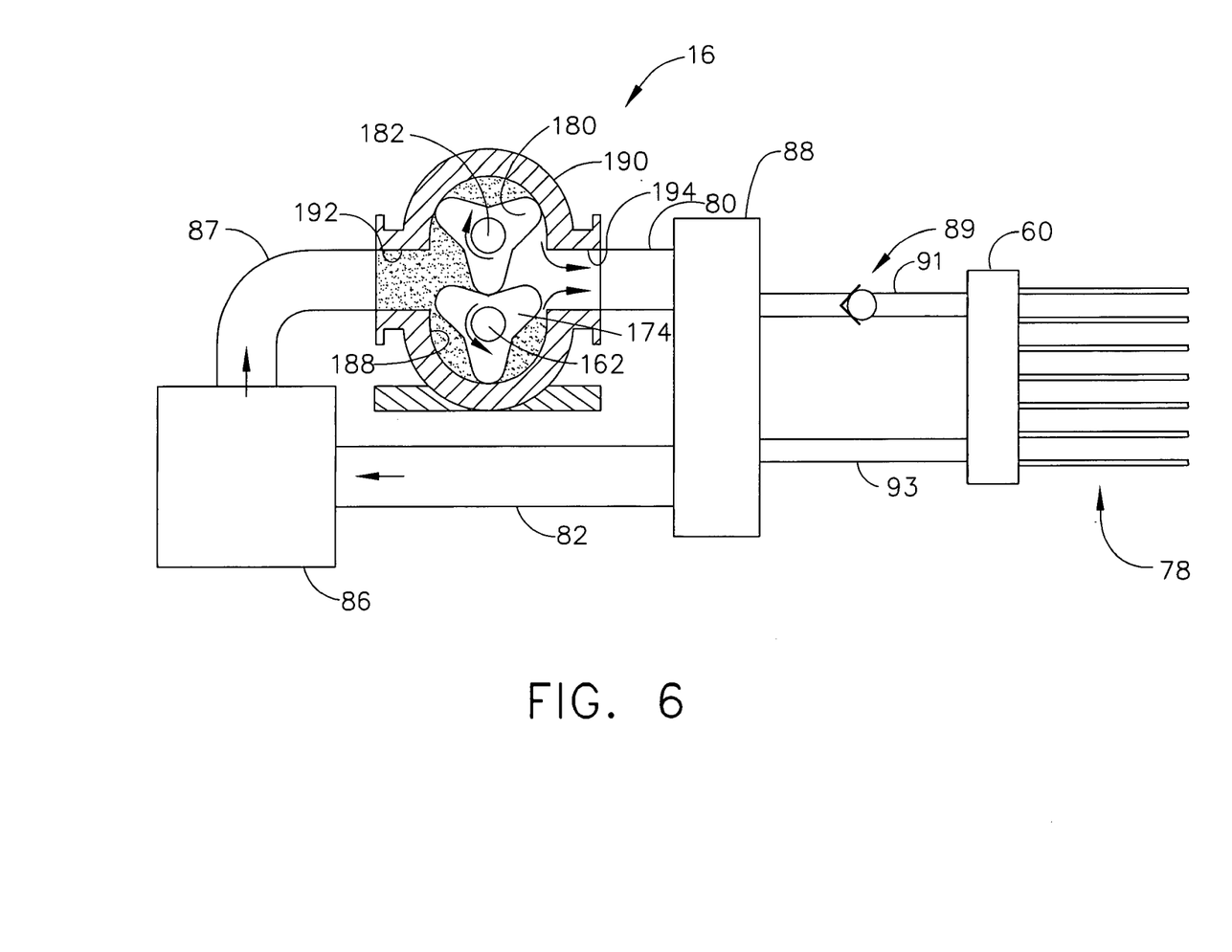
FIG. 6 is a right side diagrammatic view of the fluid control system of FIG. 1 incorporating the rotary lobe pump of FIG. 5.

In FIGS. 4, 6, the lobe members 174, 180 each have three lobes. During firing stroke of the firing trigger 22 (FIG. 4), the gear segment 130 moves distally, turning the pump drive gear 160 counter clockwise (CCW) when viewed from the right. The ratchet gear 168 is coupled in this direction of rotation and turns the primary pump shaft 162 and thus the primary lobe member 174 CCW. One upward most lobe of the primary lobe member 174 maintains contact with the secondary lobe member 180 turning the latter clockwise (CW) when viewed from the right. Each lobe member 174, 180 maintains at least one lobe in contact with a respective lower and upper proximate semi-circular inner surface of the oval pump cavity 188, distally driving a volume of fluid while in contact. Thus fluid is drawn from intake line 87 through the aft port 192 into the oval pump cavity 188 with about half being propelled by the primary lobe member 174 and about half being propelled by the secondary lobe member 180 distally through forward port 194 to the discharge line 80.

Figure 7:
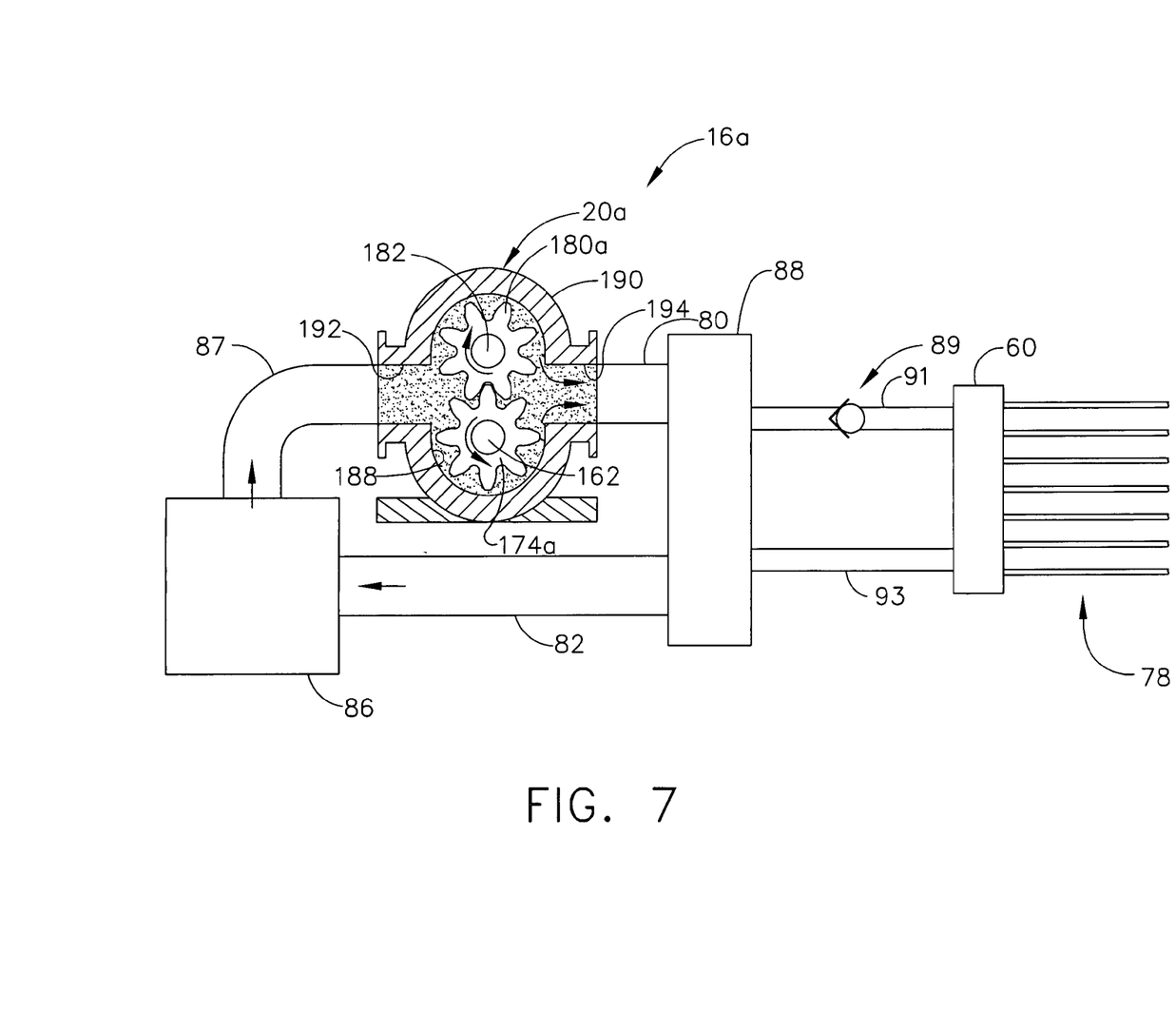
FIG. 7 is a right side diagrammatic view of the fluid control system of FIG. 1 incorporating an alternative rotary gear pump.

In FIG. 7, an alternative rotary gear pump 20a for a fluid control system 16a replaces the lob members with a primary pump gear 174a and a secondary pump gear 180a that propel fluid as otherwise described above.

Figure 8:
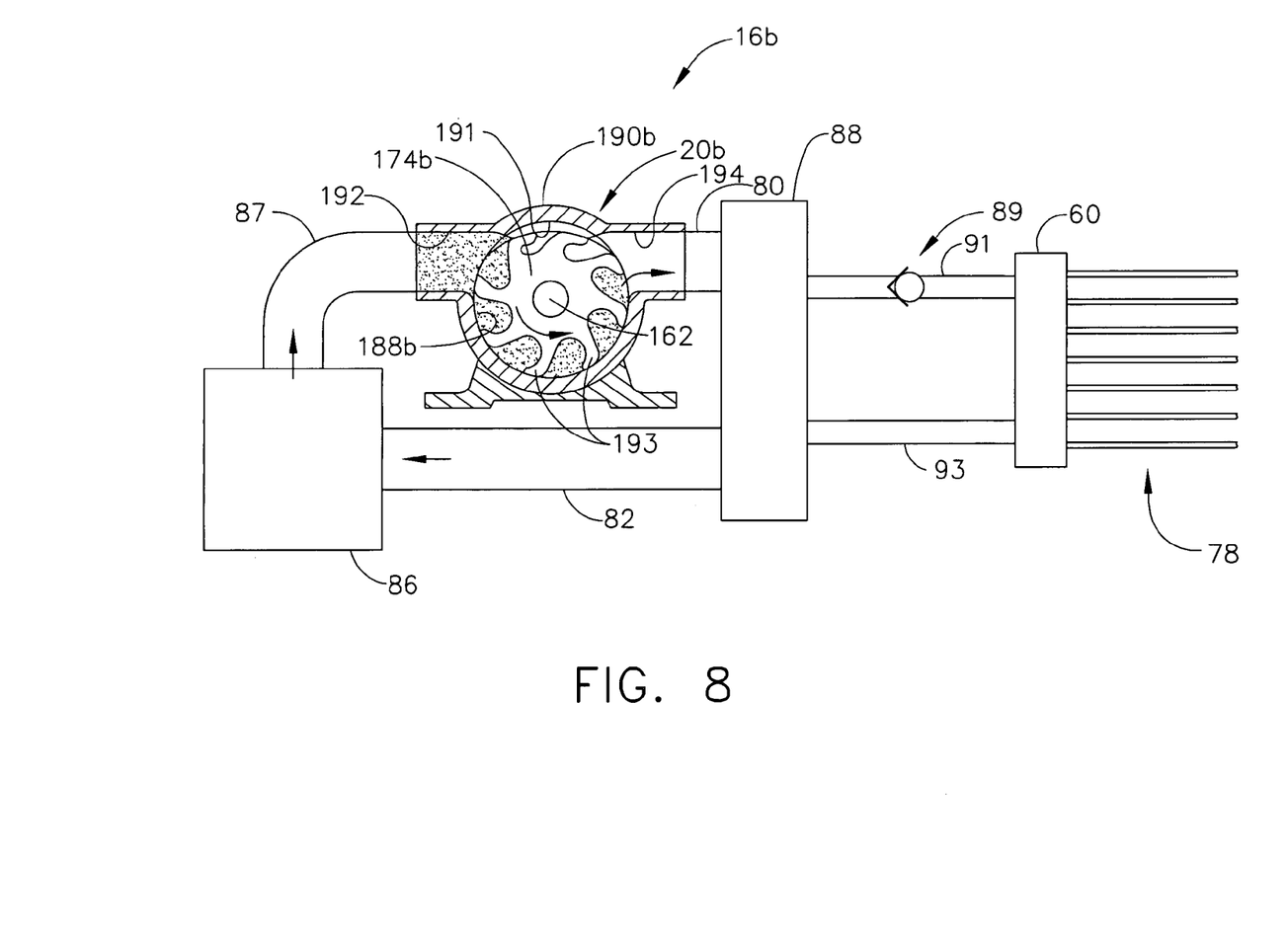
FIG. 8 is a right side diagrammatic view of the fluid control system of FIG. 1 incorporating an alternative flexible member rotary pump.

In FIG. 8, an alternative flexible member rotary pump 20b for a fluid control system 16b replaces the lob members and pump gears with a rotary flexible member 174b that resides within a generally circular pump cavity 188b within a valve body 190b. A reduced radius contoured portion 191 along a top interior portion of the generally circular pump cavity 188b compresses flexible arms 193 as the rotary flexible member rotates CCW as viewed from the right from the forward port 194 to the aft port 192. Thereby, a reduced amount of fluid is drawn proximally as compared to the distally moving flexible arms 193 moving from the aft port 192 to the forward port 194 to dispel fluid.

Figure 9:
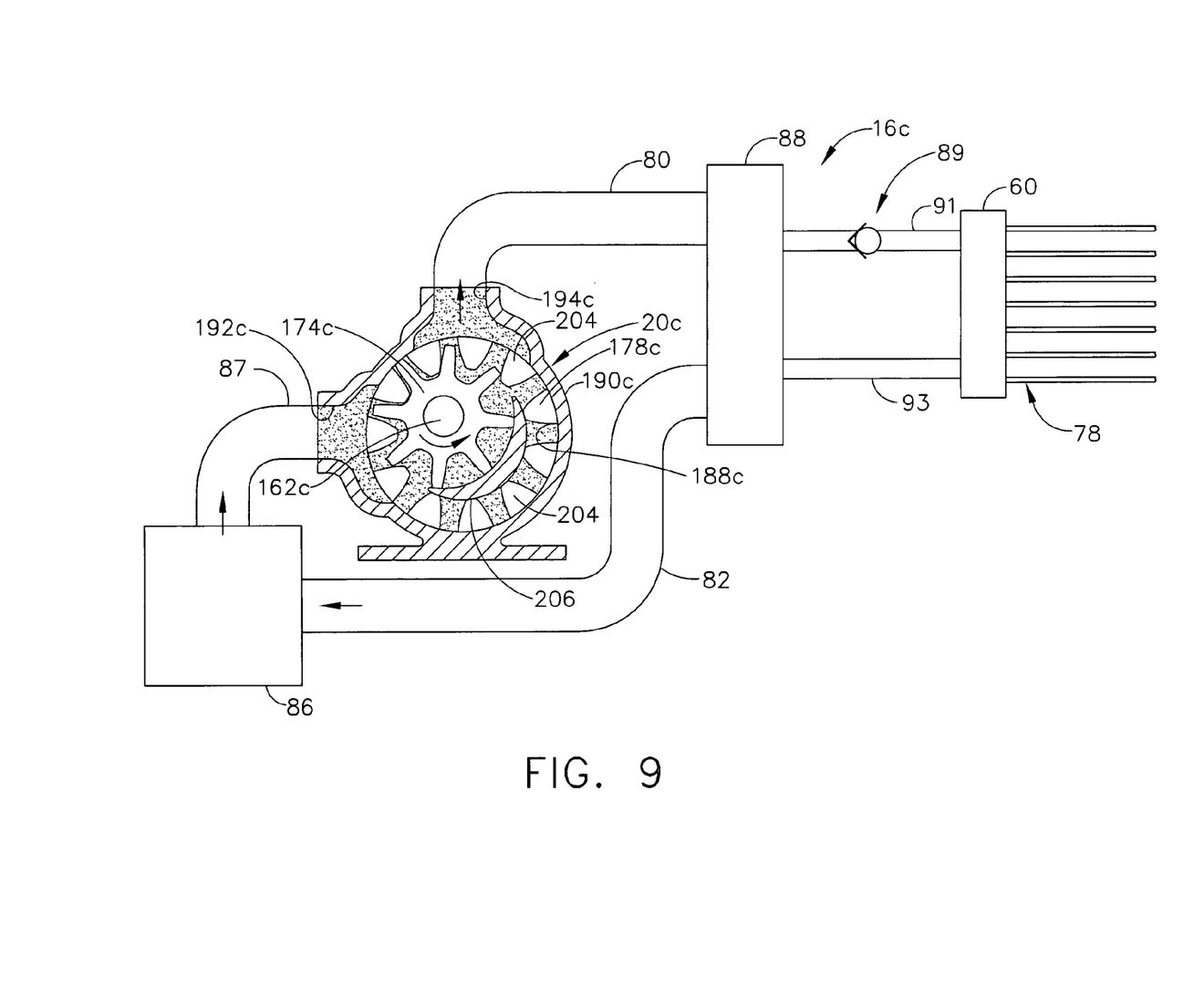
FIG. 9 is a right side diagrammatic view of the fluid control system of FIG. 1 incorporating an alternative internal gear rotary pump.

In FIG. 9, an alternative internal rotary gear pump 20c for a fluid control system 16c has an internal pump gear 174c that resides within a circular pump cavity 188c within a valve body 190c. An aft (intake) port 192c and a top (discharge) port 194c are approximately 90 degrees from one another and each have a widened communicating portion respectively with the pump cavity 188c. A left-side rotating circular pump cover plate 178c has internally projecting gear lobes 204 spaced to enmesh with the internal pump gear 174c along a top aft portion between the aft and top ports 192c, 194c. The internal pump gear 174c is driven by a pump shaft 162c that is offset closer to the top aft portion between the aft and top ports 192c, 194c, with a curved ramp 206 inwardly extending from a right-side pump cover plate (not shown) that is radially equidistant and oppositely positioned. Thus, fluid from the aft (intake) port 192c enters the circular pump cavity 188c between the gear lobes 204 and is moved CCW to the top (discharge) port 194c and dispelled, prevented from continuing around the circular pump cavity 188c by the internal pump gear 174c enmeshing with that portion of the gear lobes 204.

Figure 10:
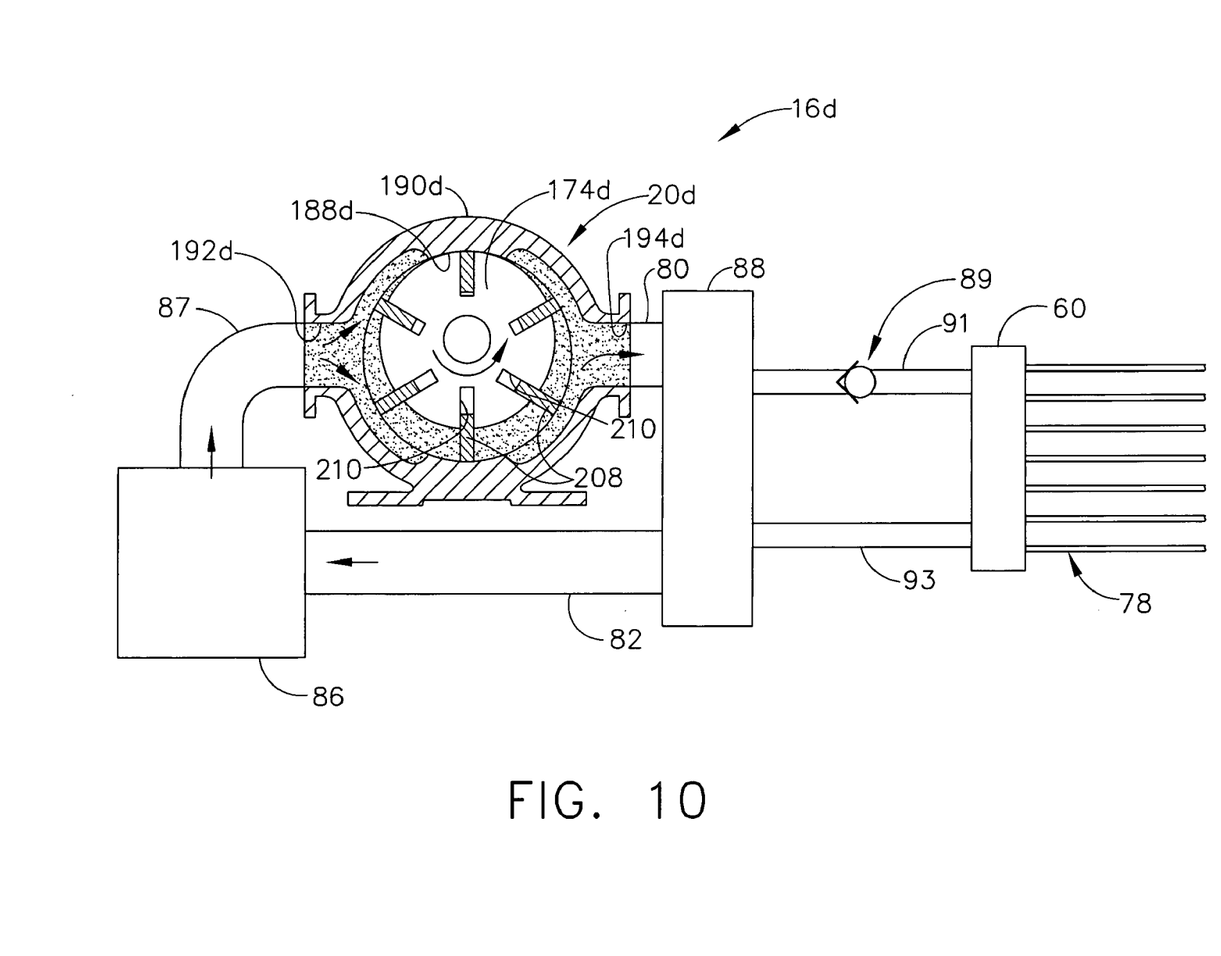
FIG. 10 is a right side diagrammatic view of the fluid control system of FIG. 1 incorporating an alternative rotary vane pump.

In FIG. 10, an alternative rotary vane pump 20d for a fluid control system 16d has an off-center cylindrical rotor 174d that resides within a circular pump cavity 188d within a valve body 190d. A plurality of radially spaced vanes 208 move within respective vane slots 210 formed in the rotor 174d. Centripetal force and/or a spring bias urges each vane 208 outward into contact with an inner diameter of the circular pump cavity 188d. Thus, fluid is drawn from an aft (intake) port 192d into an increasing volume defined between a pair of adjacent vanes 208, the rotor 174 and the inner diameter of the circular pump cavity 188d and is swept across a bottom hemispheric arc to a forward (discharge) port 194d, and is forced out as the rotor 174d contacts a top portion of the inner diameter of the circular pump cavity 188d.

Figure 11:
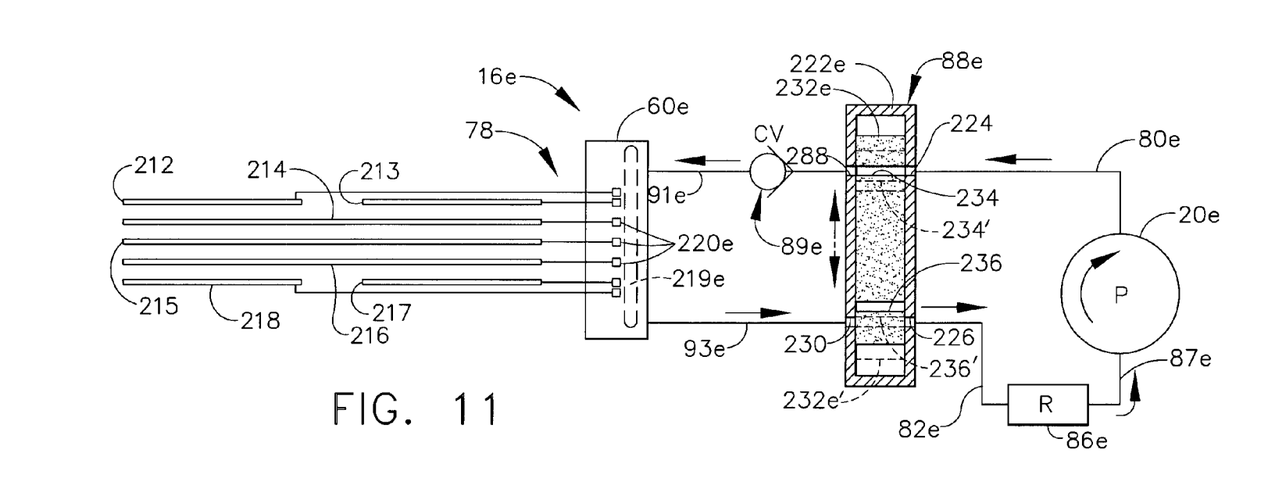
FIG. 11 is a left side diagrammatic view of a rotary pump powered fluid control system of FIG. 1 with self-deflating hydraulic subsystems.

In FIG. 11, a fluid control system 16e that incorporates a rotary pump 20e (e.g., lobe, gear flex rotor, vane, internal gear) supports a plurality of one-way, self-deflating hydraulic subsystems 212–218, each selectively opened to an internal manifold 219e of a function switch block 60e by a respective electrically actuated control valve 220e. The internal manifold 219e is in fluid communication with a feed line 91e that is selectively opened by a check valve 89e. For example, a passive check valve 89e may prevent back flow between firing strokes. As another example, an active check valve 89e may be selectively closed (e.g., default to closed position when deactivated) such that a higher upstream pressure is blocked as an additional layer of safety. The internal manifold 219e is also in communication with a return line 93e.

A return valve assembly 88e includes a valve body 222e having an upper input port 224 attached to a discharge line 80e from the rotary pump 20e. The valve body 222e has a lower input port 226 attached to a return line 82e that refills a reservoir 86e that in turn dispenses into an intake line 87e into the rotary pump 20e. The valve body 222e has an upper output port 228 attached to an input side of the check valve 89e via the feed line 91e. The valve body 222e has a lower output port 230 that is attached to receive fluid from the return line 93e. A valve shuttle 232e that moves within the valve body 222e includes an upper passage 234 that communicates between the upper input and output ports 224, 228 in a first position (depicted) and does not communicate in a second position of the shuttle (depicted in phantom at 232e', 234', respectively). The valve shuttle 232e includes a lower passage 236 that does not communicate between the lower input and output ports 226, 230 in the depicted first position but does in a second position (depicted in phantom at 236'). The valve shuttle 232e may be positionable in a third position in which both passages 234, 236 do not communicate. Alternatively or in addition, the valve shuttle 232 may have a fourth position in which an isolation passage (not shown) communicates between the upper and lower input ports 224, 226 to allow the rotary pump 20e to pump in isolation.

Figure 12:
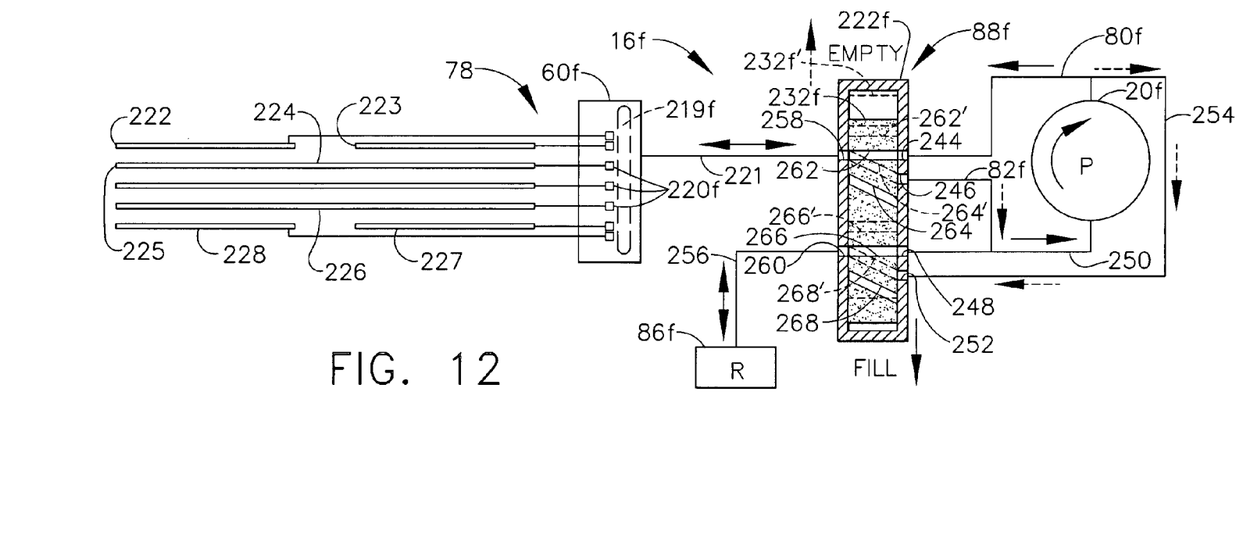
FIG. 12 is a left side diagrammatic view of a rotary pump powered fluid control system of FIG. 1 with non-self-deflating hydraulic subsystems.

In FIG. 12, a fluid control system 16f that incorporates a rotary pump 20f (e.g., lobe, gear flex rotor, vane, internal gear) supports a plurality of one-way, non-self-deflating hydraulic subsystems 222–228, each selectively opened to an internal manifold 219f of a function switch block 60f by a respective electrically actuated control valve 220f. The internal manifold 219f is in fluid communication with a first transfer line 221.

A return valve assembly 88f includes a valve body 222f having a first input port 244 attached to a first discharge line 80f from a discharge side of the rotary pump 20f. The valve body 222f has a second input port 246 attached to a first return line 82f that is coupled to an intake side of the rotary pump 20f. The valve body 222f has a third input port 248 attached to a second discharge line 250 to the intake side of the rotary pump 20f. The valve body 222f has a fourth input port 252 that communicates with a second discharge line 254 from the discharge side of the rotary pump 20f. The valve body 222f has an upper output port 258 attached to the first transfer line 221. The valve body 222f has a lower output port 260 that is attached to a second transfer line 256 that is attached to a reservoir 86f. A valve shuttle 232f that moves within the valve body 222f between a depicted first position and a second position (depicted in phantom at 232f') includes a first passage 262, a second passage 264, a third passage 266, and a fourth passage 268. When the valve shuttle 232f is in a depicted first position, the first passage 262 communicates between the first input port 244 and the upper output port 258 and the third passage communicates between the third input port 248 and the lower output port 260. Thereby the rotary pump 20f pumps fluid from the reservoir 86f to the function switch block 60f. When the valve shuttle 232f is in the second position, the second passage 264' communicates between the second input port 246 and the upper output port 258 and the fourth passage 268' communicates between the fourth input port 252 and the lower output port 260. Thereby, the rotary pump 20f pumps fluid from the function switch block 60f to the reservoir 86f.

By virtue of the foregoing, it should be appreciated that the surgical stapling and severing instrument 10 may benefit from having one actuation lever (i.e., firing trigger 22) optimized for a desired mechanical advantage. In particular, rather than resisting one motion with another mechanism, the valve unit (function switch block) 60 provides the control and the rotary pump 20 may advantageously be applied to a subset (e.g., one) of the hydraulic subsystems represented by hydraulic conduits 78. The fluid control system 16 may have a neutral position, such as provided by return valve assembly 88, that allows cycling the firing trigger 22 without effect. Another advantage is having a reservoir 86 for the entire fluid control system 16 that is encompassed within the handle 18, enabled by having a hydraulic circuit rather than a paired master-slave hydraulic cylinder arrangement. The rotary pump 20 provides the requisite amount of fluid, perhaps over a shorter or longer number of pump rotations depending upon the needs of the particular end effector actuator and need not be tuned to this amount. For example, a function requiring a significant amount of power may receive a large volume of fluid over multiple firing strokes.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, as used herein, the terms "end effector" and "surgical implement" refer to a component or set of components configured to engage tissue to accomplish a surgical task. Consistent with aspects of the present invention, surgical implements may include, but are not limited to: endocutters, graspers, clamps, cutters, staplers, clip appliers, probes or access devices, drug/gene therapy delivery devices, energy devices such as ultrasound, RF, or laser devices, etc.

As an additional example, while separate closure and firing triggers are depicted for a surgical stapling and severing instrument, applications consistent with aspects of the present invention may include a single trigger that sequentially closes the jaws upon tissue and then fires the staple applying assembly, either or both actions hydraulically powered by a rotary pump driven by the single trigger.

As another example, while a manually positioned handle and a manually depressed trigger is depicted in the illustrative version, applications consistent with the present invention may include a robotically positioned proximal portion that is not shaped for grasping by a human hand. Alternatively or in addition, an actuator, either manually moved or remotely powered, may drive the rotary pump.

As yet a further example, while a plurality of hydraulic subsystems are depicted in the illustrative versions herein, it should be appreciated that applications consistent with aspects of the present invention may include a single hydraulically actuated subsystem.

As another example, while electrical control circuitry is illustrated for selectively utilizing the hydraulic pressure from a rotary pump, applications consistent with the present invention may advantageously incorporate a fluidic control circuit that utilizes fluid pressure to process a fluidic control signal through a fluidic logic circuit to perform functions such as delaying pressure to certain hydraulic circuits as compared to others or to lockout operation unless certain conditions precedent are detected.

What is claimed is:

1. A surgical instrument, comprising:
   an elongate implement portion;
   a first hydraulic actuator positioned in the elongate implement portion;
   a handle attached to the elongate implement portion, comprising:
      a hand actuator,
      a reservoir, and
      a rotary pump contained in the handle, operated by the hand actuator, and in fluid communication between the first hydraulic actuator and the reservoir to effect fluid transfer.

2. The surgical instrument of claim 1, wherein the hand actuator comprises a trigger, the handle further comprising a ratchet mechanism operatively configured to couple the trigger to the rotary pump during a portion of reciprocal travel of the trigger.

3. The surgical instrument of claim 1, wherein the rotary pump comprises a lobe pump.

4. The surgical instrument of claim 1, wherein the rotary pump comprises a gear pump.

5. The surgical instrument of claim 1, wherein the rotary pump comprises a flexible member rotary pump.

6. The surgical instrument of claim 1, wherein the rotary pump comprises a vane rotary pump.

7. The surgical instrument of claim 1, wherein the rotary pump comprises an internally rotating gear pump.

8. The surgical instrument of claim 1, further comprising a second hydraulic actuator positioned in the elongate implement portion and a fluid control system comprising a function switch block in fluid communication with and interposed between the rotary pump and the first and second hydraulic actuators.

9. The surgical instrument of claim 8, wherein the fluid control system further comprises control circuitry operatively configured to selectively enable the function switch block.

10. The surgical instrument of claim 9, wherein the function switch block comprises a plurality of electrically actuated valves selectively allowing transfer of fluid respectively with the first and second hydraulic actuators.

11. The surgical instrument of claim 10, wherein the plurality of electrically actuated valves each comprise an electroactive polymer actuator.

12. The surgical instrument of claim 10, wherein the plurality of electrically actuated valves each comprise a piezoelectric actuator.

13. The surgical instrument of claim 1, further comprising a return valve assembly in fluid communication between a discharge port and an intake port of the rotary pump.

14. The surgical instrument of claim 13, wherein the return valve assembly is operatively configured to selectively couple the first hydraulic actuator to the discharge port of the rotary pump.

15. The surgical instrument of claim 13, wherein the return valve assembly is operatively configured to selectively couple the first hydraulic actuator to the intake port of the rotary pump.

16. The surgical instrument of claim 13, wherein the return valve assembly is operatively configured to selectively couple the discharge port to the intake port of the rotary pump bypassing the first hydraulic actuator.

17. The surgical instrument of claim 1, wherein the first hydraulic actuator comprises a self-deflating actuator.

18. The surgical instrument of claim 1, wherein the first hydraulic actuator comprises a non-self-deflating actuator.

19. A surgical instrument, comprising:
   an elongate implement portion;
   a plurality of hydraulic actuators positioned in the elongate implement portion; and
   a handle attached to the elongate implement portion, comprising:
      an actuator,
      a reservoir,
      a rotary pump contained in the handle, operated by the actuator, and in fluid communication between the first hydraulic actuator and the reservoir to effect fluid transfer; and
      a fluid control system comprising a hydraulic switching apparatus and a plurality of hydraulic conduits communicating between each of the plurality of the hydraulic actuator and the hydraulic switching apparatus.

20. A surgical instrument, comprising:
   an elongate implement portion;
   a plurality of hydraulic actuators positioned in the elongate implement portion;
   a plurality of hydraulic conduits attached at one end respectively to a selected one of the plurality of hydraulic actuators and communicating to a proximal end of the elongate implement portion; and
   a handle attached to the elongate implement portion, comprising:
      a hydraulic switching apparatus in communication with each of the plurality of hydraulic conduits,
      a trigger,
      a reservoir,
      a rotary pump contained in the handle, operated by the trigger, and in fluid communication between the hydraulic switching apparatus and the reservoir to effect fluid transfer; and
      control circuitry operatively configured to selectively control the hydraulic switching apparatus.

* * * * *